(12) United States Patent
Fuhrer (10) Patent No.: US 9,302,925 B2
(45) Date of Patent: Apr. 5, 2016

(54) METHODS FOR THE BIOREMEDIATION OF PETROLEUM IN AN AQUATIC ENVIRONMENT

(71) Applicant: John P. Fuhrer, Newport Beach, CA (US)

(72) Inventor: John P. Fuhrer, Newport Beach, CA (US)

( * ) Notice: Subject to any disclaimer, the term of this patent is extended or adjusted under 35 U.S.C. 154(b) by 193 days.

(21) Appl. No.: 14/223,863

(22) Filed: Mar. 24, 2014

(65) Prior Publication Data

US 2014/0284272 A1    Sep. 25, 2014

Related U.S. Application Data

(62) Division of application No. 13/274,318, filed on Oct. 15, 2011, now Pat. No. 8,679,820.

(60) Provisional application No. 61/393,867, filed on Oct. 15, 2010.

(51) Int. Cl.
*C02F 3/34* (2006.01)
*C12N 1/26* (2006.01)
*C02F 101/32* (2006.01)

(52) U.S. Cl.
CPC . *C02F 3/343* (2013.01); *C12N 1/26* (2013.01); *C02F 2101/32* (2013.01)

(58) Field of Classification Search
None
See application file for complete search history.

(56) References Cited

U.S. PATENT DOCUMENTS

| | | | | |
|---|---|---|---|---|
| 5,679,364 A | * | 10/1997 | Levy | B09C 1/00 424/405 |
| 2003/0134409 A1 | * | 7/2003 | Mallouk | B01J 20/20 435/262.5 |
| 2003/0232965 A1 | * | 12/2003 | Bergeron | A61K 8/64 530/300 |

* cited by examiner

*Primary Examiner* — Tracy Vivlemore
*Assistant Examiner* — Monica Shin
(74) *Attorney, Agent, or Firm* — Alford Law Group, Inc.; William E. Alford; Vy H. Vu (57) ABSTRACT

In one embodiment, a bioremediation agent and method of bioremediation of an oil spill are disclosed. The bioremediation agent contains oil-digesting bacteria and bacterial nutrients in a buoyant water semi-insoluble and biodegradable casein product. The bioremediation agent may be distributed by boats or seeded by aircraft to remediate oil from coastlines after an oil spill.

19 Claims, 7 Drawing Sheets

METHODS FOR THE BIOREMEDIATION OF PETROLEUM IN AN AQUATIC ENVIRONMENT

CROSS REFERENCE TO RELATED APPLICATIONS

This patent application is a division of, incorporates by reference, and claims the benefit of U.S. patent application Ser. No. 13/274,318 "METHOD AND AGENT FOR THE BIOREMEDIATION OF PETROLEUM IN AN AQUATIC ENVIRONMENT" filed on Oct. 15, 2011 by inventor John Peter Fuhrer, which in turn claims the benefit of Provisional Patent Application No. 61/393,867, also entitled "METHOD AND AGENT FOR THE BIOREMEDIATION OF PETROLEUM IN AN AQUATIC ENVIRONMENT" filed on Oct. 15, 2010 by inventor John Peter Fuhrer.

FIELD

Aspects of the invention generally relate to a method and a composition of matter for removing petroleum. More specifically, aspects of the invention relate to a method and a composition of matter for oil removal utilizing an oil-digesting bacteria combined with a nutrient source in a biodegradable product capable of being distributed over a large target area.

BACKGROUND

Petroleum is ubiquitous to the modern age. Petroleum is directly used as a fuel source e.g. oil, natural gas, and gasoline or indirectly used in products such as plastics, tar, and asphalt. In a global economy where commodities and products must be transported thousands of miles from their source to market, fossil fuels are an important natural resource.

Global petroleum usage usually increases each year. Most of the global petroleum consumption is concentrated in developed countries such as the United States, Japan, and Germany. Consumption in developing countries with large manufacturing bases such as China and India is increasing at a rapid rate. China, with its large population and growing middle class has surpassed Japan as the world's second largest consumer of petroleum products.

Although the U.S., China, and Japan are presently the three largest consumers of oil, they do not produce all of the oil they consume. Some of the oil consumed in these nations is imported. Oil production in most developed countries is falling. A large percentage of the world's proven oil reserves are located in the Middle East. Thus, with demand increasing and local supply of oil dwindling, it is likely that consumer nations will continue to import large quantities of oil in the future.

The widespread use of petroleum has many harmful side effects. Air, ground, and water pollution have caused the extinction of numerous species of plants and animals. Many petroleum by-products are also carcinogenic. The burning of petroleum as a fuel source has increased atmospheric carbon dioxide, leading to a green house effect and global warming. Besides the expected harmful aspects, widespread petroleum usage also leads to inevitable accidents. With billions of barrels extracted and transported annually, oils spills occur frequently.

Oil spills in the worlds oceans, are the inevitable result of the extraction and transportation of vast quantities of oil. Oil spills resulting from the grounding of an oil tanker or an explosion aboard an offshore oil rig, may cause hundred of millions of dollars in loss to the local fishing and tourism industries. Oil spills can also result in long term ecological damage to coastal areas where they occur.

Oil spills occurring in or near a body of water are difficult to contain and cleanup. Tides and currents spread spilled oil over a large area making containment difficult. Inclement weather may also make deploying booms or other barriers difficult. Cleanup is further inhibited due to the sensitive habitats in or adjacent to water. For instance, plants and animals inhabiting coral reefs, wetlands, estuaries, marshes and mangroves are extremely sensitive to pollution and may die off quickly before a cleanup response can be initiated. Furthermore, coastal waters contain vast numbers of drifting plankton composed of fish eggs and larvae at the bottom of the food chain. These are often killed by toxic oil compounds and dispersants. Alternatively, plankton may be caught in oil tar balls and become inedible to fish.

Although more can be done to prevent oil spills into a body of water from occurring in the first place, oil spills are going to occur as long as the world depends on petroleum as a main source of fuel. So long as cars run on gasoline and airplanes require jet fuel, there exists a need for an effective way to remove oil quickly and efficiently from our oceans with low impact on the environment.

Known methods of cleaning an oil spill in water generally rely on booms to contain the spill, followed by burning or skimming to remove the spilled oil. However, booms may be ineffective due to inclement weather. Burning the oil causes air pollution. Skimming the oil is labor and equipment intensive.

Another method of cleaning an oil spill involves spraying chemical dispersants on the surface oil. Dispersants may also be released at the source of an underwater oil leak. The drawback of chemical dispersant use is that the dispersants themselves are often toxic to plant and animal life. Furthermore, use of dispersants may actually prevent burning and skimming of the oil because the oil is no longer in sufficient concentration to be skimmed or burned.

Thus what is needed are methods and agents for cleaning oil spills that are more effective and environmentally friendly. The desired agents could be deployed over sensitive ecosystems quickly and relatively inexpensively.

BRIEF SUMMARY

The embodiments of the invention are best summarized by the claims that follow below. However, briefly, in accordance with aspects of embodiments of the invention a bioremediation agent and methods of petroleum remediation using said agent are disclosed. The bioremediation agent includes oil-digesting bacteria suspended in a biodegradable product with nutrients. The bioremediation agent is deployed to aid in the cleanup of an oil spill.

The figures are not drawn to scale so that elements, features, and surface structure may be shown by example and are intended merely to be illustrative and non-limiting of the aspects of the invention that are claimed.

DETAILED DESCRIPTION

This detailed description describes exemplary implementations that are illustrative of aspects of the invention, and so it is explanatory and not limiting. The claims define inventive aspects. In the drawings, some elements have been omitted to more clearly show inventive aspects.

Introduction

Oil-digesting bacteria (may also be referred to as oil-eating bacteria) exist in nature. They are normally found in soil especially near surface level petroleum such as tar pits. An oil spill occurring on land can be quickly contained and cleaned. Residual oil will eventually be digested by naturally occurring oil-digesting bacteria in the soil.

Unfortunately, catastrophic oil spills also occur in aquatic regions. An aquatic oil spill generally spreads at a rapid rate due to currents and tides. Sensitive habitats such as fish hatcheries, delicate wetlands, estuaries, tourist havens and fishing grounds are often near an oil spill. Therefore, it is desirable to clean up aquatic oil spills rapidly and with minimal impact to the surrounding area.

Aquatic oil spills may also cause more damage because the naturally existing oil-digesting bacteria are not concentrated in water. The ocean is not ideally suited for bacterial growth. Cold temperatures, lack of nutrients, and constant agitation from wind and tidal motion tend to inhibit bacteria growth. Thus, naturally occurring oil-digesting bacteria will likely be in low concentration and in isolated patches, for example, near underwater oil seeps in the sea floor. Engineered oil-digesting bacteria may be formed to digest oil but may be less favorable to use due to potential unpredicted environmental consequences.

Bioremediation Agent

A bioremediation agent and methods of petroleum remediation using said agent are disclosed. Bioremediation has been used successfully to mitigate previous oil spills. However, the distribution of oil-digesting bacteria has been difficult to control to ensure that the bacteria remain in contact with the oil. Improving the contact between oil-digesting bacteria and oil is one of the goals of the embodiments of the invention.

Figure 1A:
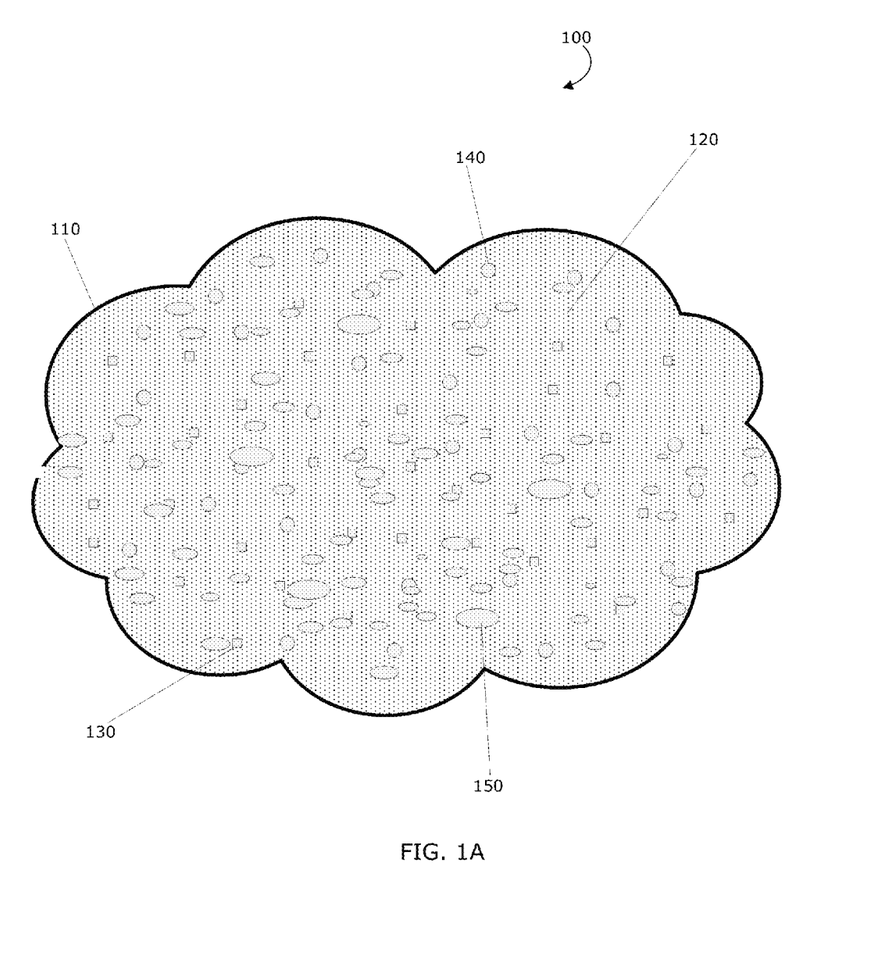
FIG. 1A is a magnified top view of an embodiment of the invention illustrating a product including oil-digesting bacteria.

Referring now to FIG. 1A, an embodiment of a bioremediation agent 100 is illustrated. The bioremediation agent 100, a composition of matter, includes a product 110, oil-digesting bacteria or bacterium 120, bacterial nutrients 130, one or more air pockets or bubbles 140, and micro-pores 150. The oil-digesting bacterium 120 digests oil when it makes contact with the oil of an oil spill received in the micro-pores and at the perimeter of the agent 100. The bioremediation agent 100 may be deployed at a target site where an oil spill has occurred to digest the oil and clean up the spilled oil.

The product 110 is biodegradable, non-toxic, semi-insoluble, and easily manufactured. The air pockets or bubbles 140 may be suspended in the product 110 to aid in buoyancy and float the bioremediation agent 100 near oil located at the water surface. Micro-pores 150 throughout the product 110 allow oil to be absorbed into the agent 100 so that it is in closer contact with the oil-digesting bacteria 120. Alternatively, incorporation into agent 100 of an inert material with a specific gravity greater than water (e.g., sand, silt, mud, sediment) may be used to sink the bioremediation agent to oil located below the surface of the water. Also suspended in the product 110 are the oil-digesting bacterium 120 and the bacterial nutrient 130. The bacterial nutrient 130 is used to promote reproduction of the bacterium 120 so more oil may be digested.

In one embodiment of the invention, the product 110 is a casein product. Casein is a water soluble biodegradable protein found in mammalian milk. When in milk, casein occurs as a suspension of particles called micelles. A typical micelle in aqueous solution forms an aggregate with the hydrophilic "head" regions in contact with surrounding solvent, sequestering the hydrophobic tail regions in the micelle center.

Casein may be isolated from milk by several methods. Casein can be precipitated from milk by an enzymatic method or by a mild acid treatment method, for example.

However, it is desirable to make proteins semi-insoluble in water so that the product slowly dissolves in water over a predetermined period of time so that the unused protein and bacteria are digested. Various methods may be used to produce semi-insoluble protein material that can be formed into shapes and can be made to contain many types of components. One such method for casein protein is described in U.S. Pat. No. 6,379,726 issued to Peggy Tomasula on Apr. 30, 2002 and U.S. Patent Application Pub. No. 2004/0018294 filed by Peggy Tomasula on Feb. 10, 1999, both of which are incorporated herein by reference. Alternatively, other methods may be used to link or cross-link proteins, such as by a chemical approach, an aging approach, or some other molecule alignment process so the protein molecules are aligned to resist being fully soluble in water and allow a predetermined period of time for the oil-digesting bacteria to digest the oil before dissolving into water and/or biodegrading.

The casein product 110 may be formed into any shape. In one embodiment of the invention the casein product 110 may take the shape of a flake. The flakes may be small, substantially flat, thin closed curve-like shapes. Although the casein product 110 is described and illustrated as a flake, the scope of the invention covers other three dimensional shapes that are regular or irregular, such as a rectangular wafer or an irregular spherical shaped particle for example.

Casein is biodegradable and non-toxic. In a semi-insoluble form, the casein product 110 will eventually degrade or dissolve in water. Casein product 110 deployed at a spill site will biodegrade without the need for labor intensive cleaning. Unlike dispersants which are toxic to marine life, casein is an edible milk protein and thus less likely to harm marine life that may contact or eat the casein.

While the product 110 has been described as being formed of casein protein, the product may be formed of other proteins, such as soy protein, that may be made semi-insoluble and absorb or suspend the oil-digesting bacteria.

Figure 1B:
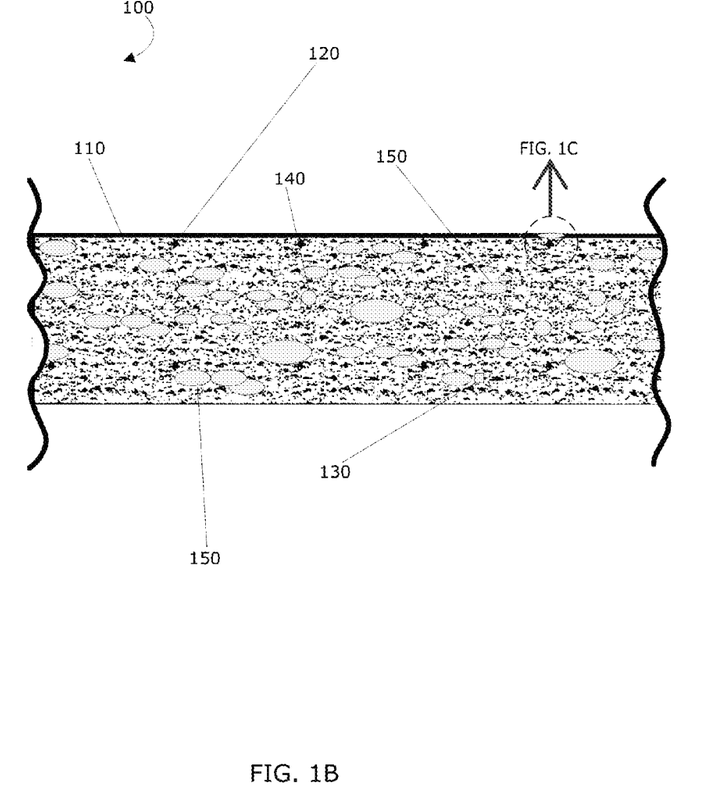
FIGS. 1B-1C are magnified cross-sectional views of the product of FIG. 1A to better illustrate the micro-pores included therein.
Figure 1C:
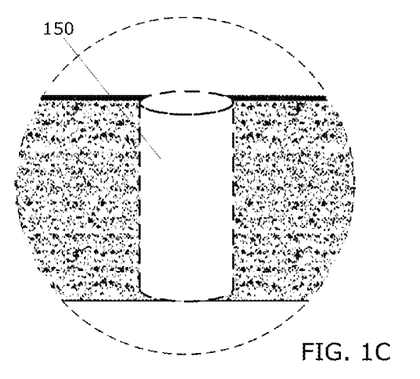

Referring now to FIGS. 1B-1C, magnified cross-section views of the product 110 are shown to better illustrate the micro-pores 150 formed in the product 110. The micro-pores 150 are small channels or tunnels within the product extending from its exterior surface to interior portions of the product 110. The micro-pores 150 increase the surface area of the product 110 where the oil-digesting bacteria 120 can make contact with oil. As the exposed surfaces of the protein product dissolve due to being semi-soluble or semi-insoluble, fresh oil-digesting bacterial may be exposed at the new surfaces to further digest oil.

Oil-digesting bacteria 120 may be randomly spread throughout the protein product 110 as shown in FIGS. 1A-1C in one embodiment of the invention. Alternatively, the oil-digesting bacteria 120 may be concentrated near the exposed surfaces and diffused into the interior portions in another embodiment of the invention.

Figure 1D:
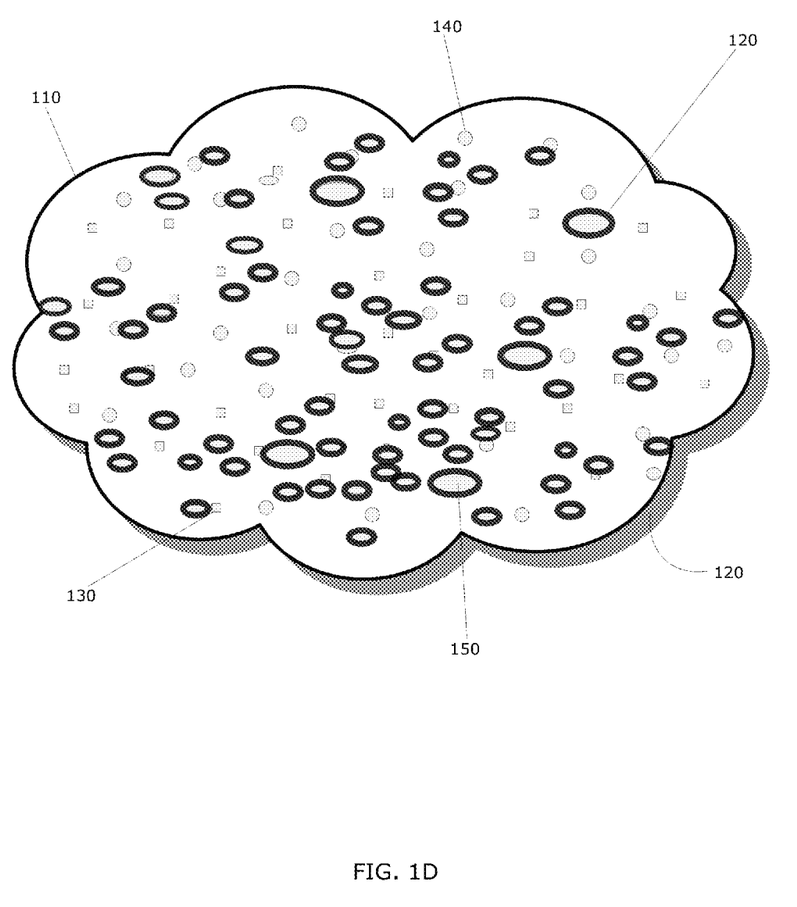
FIG. 1D is a magnified top view of an alternate embodiment of the invention illustrating a product including oil-digesting bacteria.

Referring now to FIG. 1D, a magnified top view of an alternate embodiment of the invention illustrating a product including oil-digesting bacteria 120 is shown. In this case, the oil-digesting bacteria 120 is concentrated near the exposed surfaces of the product and diffused into the interior portions. The oil-digesting bacteria 120 is concentrated around the perimeter or exterior surface of the protein product 110 as shown by the shadowing. Further oil-digesting bacteria 120 is concentrated around the walls of the micro-pores 150 as shown by the thicker lines in the drawing. The concentration of the oil-digesting bacteria 120 diffuses to a lower concentration per area at points further away from the external surface. In this case, the protein product 110 may be initially formed with micro-pores 150 and the air bubbles 140. The protein product 110 is then soaked in a bath of oil-digesting bacteria 120 so that bacteria are absorbed and diffused through the external surfaces into the interior of the product. As the exposed surfaces of the protein product dissolve due to being semi-soluble or semi-insoluble, fresh oil-digesting bacterial may be exposed at the new surfaces to further digest oil.

Petroleum oil is generally buoyant. Thus, during an oil spill much of the oil is found on the surface of the water. In one embodiment of the invention, air pockets 140 may be formed in the casein product 110 to allow the bioremediation agent 100 to float at the same water level as the oil spill. Keeping the bioremediation agent 100 in the general proximity of the oil may be advantageous. Oil-digesting bacteria need to be in contact with the oil in order to digest it. Furthermore, floating at the surface allows the bioremediation agent 100 to travel with the oil spill into remote areas, such as into and around marsh grass stems and mangrove roots, for example.

Currents and tides will move oil plumes. Oftentimes, this movement is difficult to predict because of prevailing weather conditions. Resources to protect sensitive habitats may be deployed too late or deployed to the wrong place because of unpredicted oil movement. Deploying booms in tidal areas may also be difficult. Heavy winds and high tides may move booms or even push the oil over the booms.

Furthermore, nature preserves and estuaries generally have limited access. There are usually no roads leading into these delicate eco-systems. Once an oil spill reaches land, it may be difficult to send workers into remote areas to remove the oil residue e.g. tar-balls. Heavy equipment such as bulldozers and disposal trucks may not be able to reach some areas. The use of heavy equipment may also scar the landscape for years to come.

Fortunately, bioremediation agent 100 will generally follow the path of the oil plume. Bioremediation agent 100 distributed right at the source of an oil plume may drift with the plume because it is affected by the same currents and tides. As the oil plume spreads towards shore and difficult to reach estuaries, the bioremediation agent 100 will move with the plume, so that the oil-digesting bacteria 120 may continue to digest the oil. Unlike booms and barriers, the bioremediation agent 100 will be working before reaching coastal waters. The bioremediation agent 100 is capable of floating into the more difficult to reach areas and may continue to degrade the spilled oil with little intervention.

Although, the embodiment of the invention described above contains air pockets 140 to allow the bioremediation agent 100 to float at the surface of the water, it may be possible to vary the buoyancy of the flake. After an oil spill, dispersants may be used in such large amounts that oil particles remain suspended in the ocean below the surface. Underwater plumes of suspended oil can not be skimmed or burned. Varying the buoyancy of the casein product 110 may allow the bioremediation agent 100 to travel submerged in an underwater oil plume.

Figure 2A:
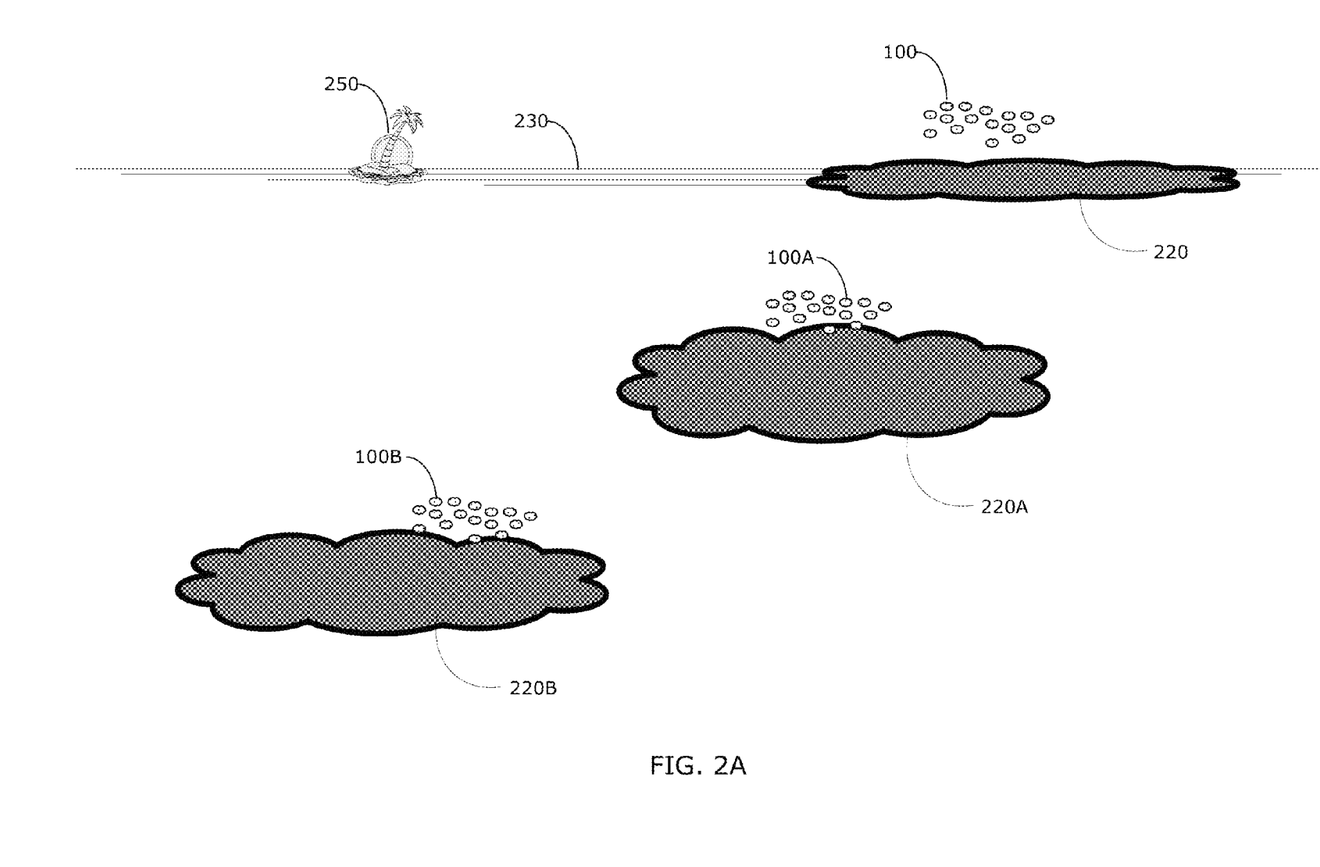
FIG. 2A is an illustration of various embodiments of the invention being used at different water depths.

Referring now to FIG. 2A, an alternative embodiment of the invention is depicted being deployed at different depths. In FIG. 2A, oil spill 220 is floating on ocean surface 230 and encroaching on tourist haven 250. Bioremediation agent 100 may be air dropped onto surface oil spill 220 before it reaches tourist haven 250. However, due to the widespread use of dispersants, submerged oil plumes 220A and 220B remain suspended below the ocean surface. Submerged oil plumes 220A and 220B may not be skimmed or burned because they exist as clouds of tiny suspended oil droplets that move with underwater currents without surfacing.

In order to combat submerged oil plumes 220A and 220B, an inert material with a specific gravity greater than water (e.g., specific gravity of fresh water in the case of an oil spill in fresh water or specific gravity of salt water in the case of an oil spill in salt water) may be used to sink the bioremediation agent 100 to reach oil located below the surface of the water. Bioremediation agent 100A and 100B are alternative embodiments of floating bioremediation agent 100 that sink to different depths of water. The buoyancy of bioremediation agent 100A may be altered so that the bioremediation agent 100A is slightly denser than surface temperature water. Generally, water is colder the deeper it gets. Colder water is denser than warm water, thus at some depth the bioremediation agent 100A reach it equivalent density and will stop sinking. Bioremediation agent 100B may be made relatively denser than bioremediation agent 100A to sink to an even lower depth. These alternative embodiments may be created by adding to bioremediation agent 100, an inert material with a specific gravity greater than water. Alternative embodiments of the bioremediation agent 100A and 100B may or may not include air pockets 140 in their makeup to achieve a desired buoyancy and depth below the water surface.

Figure 2B:
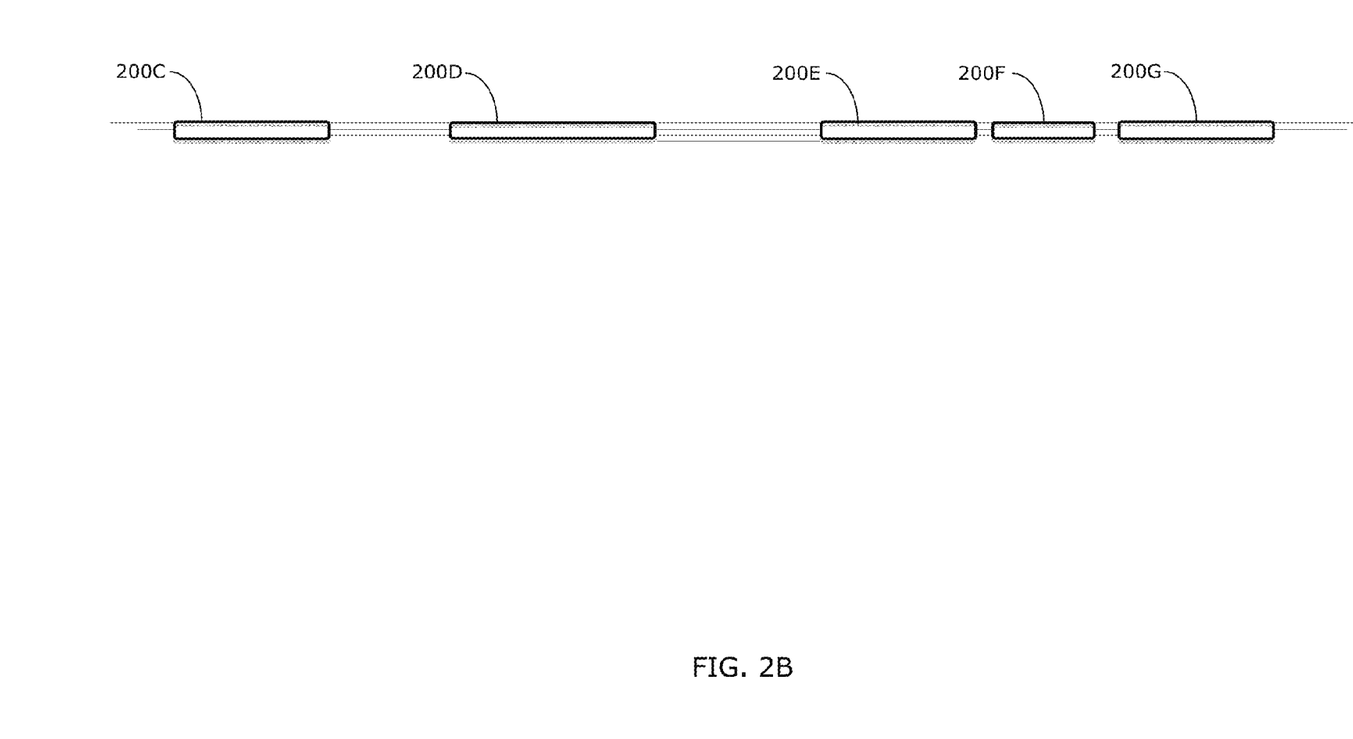
FIG. 2B is a side view an embodiment of the invention dispersed at different concentrations.

Referring now to FIG. 2B, embodiments of the invention may be deployed at different concentrations upon the surface or in the depths below the surface. FIG. 2B illustrates bioremediation agent 200C and 200D (instances of the bioremediation agent 100) deployed at a first concentration upon the surface of water. FIG. 2B illustrates bioremediation agent 200E through 200G (instances of the bioremediation agent 100) deployed at a second concentration upon the surface of water that is greater than the first concentration. An initial concentration may be estimated by how much of the bioremedial agent is deployed in a given area of an oil spill. Subsequent natural effects (e.g., waves, currents, wind) and man made effects (e.g., boat wake, propeller wash, or machine stirring or dispersing) can disperse the bioremediation agent and reduce its concentration at the surface of water or at depths in the water.

Referring now back to FIG. 1, also suspended in the casein product 110 is oil-digesting bacteria 120. An example of oil-digesting bacteria 120 is *Pseudomonas putida*. Although this bacterium is listed by name, the invention should not be considered as being limited to using only this bacterium. Other types of oil-digesting bacteria 120 may be used.

The oil-digesting bacteria 120 may be found in nature. However the concentration of oil-digesting bacteria 120 in nature is generally low. Oil-digesting bacteria 120 generally are found in areas where there is naturally occurring oil, such as underwater seepage or near pools of surface oil such as tar pits. However, even at these naturally occurring locations where oil-digesting bacteria are found, the concentration is generally too low to digest significant amounts of oil.

Like most bacteria, oil-digesting bacteria generally multiply when nutrients such as nitrogen or phosphorus are available. However, nutrients are generally limited in quantity in a marine environment. Competition from plants for nitrogen and phosphorus e.g. fertilizer also keeps nutrient quantities low.

Simply, adding fertilizer to the ocean to stimulate oil-digesting bacteria growth may have limited effects and unintended consequences. A high concentration of fertilizer may not be capable of being maintained at the oil spill site. The ocean is a vast body of water. Chemicals dissolved in the ocean tend to dilute quickly. Adding more fertilizer to an oil spill site to offset dilution may cause eutrophication, an increase in nutrients which results in an increase in the growth of the primary producers at the bottom of the food chain.

Generally the increase of a nutrient, such as nitrogen, promotes the rapid growth of simple algae and plankton over more complicated plants. Algae, plankton and the marine animals dependent on algae and plankton as a food source eventually die out because they cannot compete. The resulting decrease in bio-diversity is undesirable. Furthermore, certain algae produce biotoxins which may be taken up the food chain by shellfish and cause food poisoning. The rapid growth of algae or plankton blooms is unsustainable and the eventual die-off of the algae may cause anoxia. The decaying algae uses up dissolved oxygen until fish and other marine animals suffocate.

Sufficient levels of nutrient may be maintained at the oil spill site without promoting eutrophication by controlling and targeting the release of the nutrients. The nutrient 130 is suspended in casein product 110 in proximity with the oil-digesting bacteria 120 to support growth and proliferation of the oil-digesting bacteria suspended within the product without excessive algae growth. The suspended nutrient 130 also will not dilute as swiftly when the bioremediation agent 100 is submerged in water. As the casein product 110 is slowly solubilized by water, the nutrient 130 is released in a controlled manner in close proximity to the oil-digesting bacteria 120.

Naturally occurring oil-digesting bacteria also may be selected as the oil-digesting bacteria 120 for specific properties. For example, an oil-digesting bacteria 120 more resistant to cold temperatures may be obtained from cold regions such as Alaska for deployment at ocean depths where the water is colder.

Method of Delivery

The invention may be deployed to aid in the cleanup of an oil spill by aerial dispersal, distributed by ship, or even by hand. Use of aerial dispersal may be preferred in remote areas where ships may take days or weeks to respond to an oil spill. However, the use of ships may be preferred where large quantities of the bioremediation agent 100 may be required.

Figure 3:
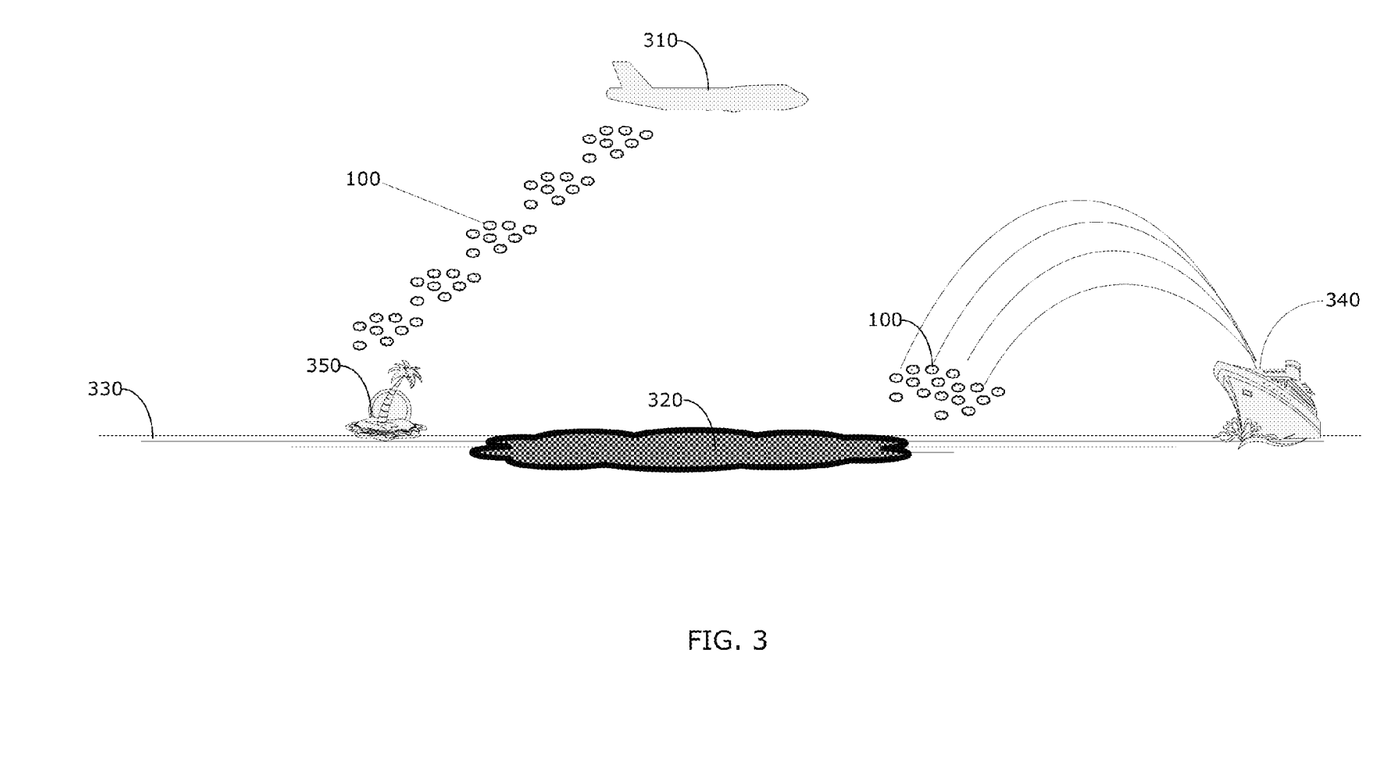
FIG. 3 is an illustration of different methods of deploying an embodiment of the invention.

Referring now to FIG. 3, an illustration of methods for deploying bioremediation agent 100 is shown. In one method of deployment, an aircraft 310 (e.g., airplane, helicopter, airship, balloon) is shown dropping bioremediation agent 100 onto oil spill 320 at the surface of the ocean 330. In another method, a ship 340 is shown dispersing bioremediation agent 100 by propelling the bioremediation agent 100 onto the oil spill 320. Although the bioremediation agent 100 is shown being propelled over the side of the ship 340, a simpler method of dropping the bioremediation agent over the side of ship 340, such as by a spreading mechanism or by hand, can achieve similar results. One or more of these and other methods of deploying the bioremediation agent 100 may be used together or individually on oil spills.

In FIG. 3, a sensitive eco-system 350 is endangered by the encroaching oil spill 320. Aircraft 310 may drop bioremediation agent 100 directly on the sensitive eco-system 350. Alternatively, bioremediation agent 100 may be manually applied onto the sensitive eco-system 350 from land, such as by hand, wheeled spreaders (e.g., a fertilizer spreader), dump trucks or spreading trucks. Bioremediation agent 100 is more environmentally friendly than chemical dispersants and will biodegrade, thus deploying bioremediation agent 100 directly onto the sensitive eco-system 350 is a viable option.

Methods of deployment may require consideration of several factors, such as type of spill, location of the spill, and amount of the spill. For example, larger spills closer to shore may be more efficiently cleaned using shipboard deployment of the bioremediation agent 100.

Aerial dispersal over wide areas may be accomplished with equipment similar to that used for dispersing flame retardants. A low flying fixed wing aircraft 310 or helicopter may be used to accurately target dispersal areas. Aircraft 310 may be capable of deploying the bioremediation agent 100 to remote areas not readily accessible to vehicles or by foot. Furthermore, aircraft may be capable of reaching a target site faster than other dispersal methods, possibly preventing or mitigating harm to sensitive eco-systems 350.

Incident Response

Figure 4:
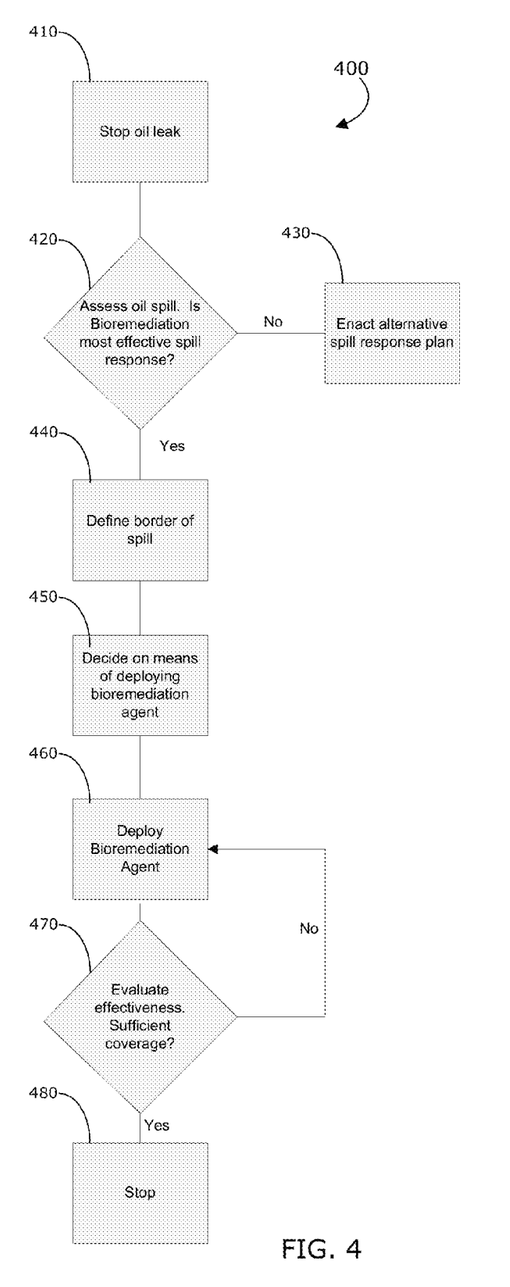
FIG. 4 is a flowchart of an exemplary spill response illustrating a method of using the invention.

Referring now to FIG. 4, an incident response flow chart 400 is shown detailing a method of using the bioremediation agent 100. The flow chart 400 lists the main actions to be taken in the event of an oil spill or an oil leak.

In process block 410, an incident commander should first stop the source of the oil leak if possible. Actions such as capping a leaking well or draining a grounded tanker may be necessary to stop the source of the spill from adding additional oil to the spill. In some circumstances it may not be feasible to completely stop an oil leak and the incident commander may need to move onto the next step of the response plan while concurrently continuing attempts to block or stop the source. The process then goes to process block 420.

At process block 420, the oil spill is accessed. Considerations such as amount of the spill, type of oil released (e.g., heavy crude, light crude, natural gases etc.), area of the spill, and location of the spill may be used to calculate an appropriate response involving bioremediation agent 100 and or other oil containment/removal methods. If deployment of bioremediation agent 100 is considered a viable option, the process continues to process block 440. If deployment of bioremediation agent 100 is not an option, the spill may be contained in a different manner and the process goes to process block 430.

At process block 430, assuming the bioremediation agent 100 is not going to be deployed, an alternative spill response plan is enacted to contain the oil spill.

At process block 440, assuming the bioremediation agent 100 is to be deployed, the boundary of the spill is determined. Observation by aircraft will likely be needed for large spills covering multiple square miles. Once the boundary is determined, the process may go to process block 450.

At process block 450, the appropriate means of deploying the bioremediation agent 100 is decided. The deployment method (e.g., by air, ship, or foot) is responsive to the observations and the decisions made previously at process blocks 420, 440. Factors such as size of spill, spill vicinity to sensitive eco-systems or tourist havens, speed and direction of currents may be considered when deciding on the means of deployment. The process then goes to process block 460.

At process block 460, the bioremediation agent 100 is deployed by the chosen method or methods. The process then goes to process block 470.

At process block 470, an evaluation is performed to determine the effectiveness of the method of deployment and the bioremediation agent 100 at digesting the oil spill. The incident commander may evaluate if the spill was sufficiently covered. In areas where the spill is densest, more bioremediation agent 100 may be needed. If the deployment of the bioremediation agent 100 was insufficient or ineffective, the process returns to process block 460 to deploy additional bioremediation agent 100 by the same or different method of deployment. If the bioremediation agent 100 is effective, the process goes to process block 480 and ends.

A processor of a computer with a storage device coupled thereto may be used to execute instructions stored in the storage device to perform or cause to perform, the one or more of the processes of the incident response to the oil spill.

Conclusion

While this specification includes many specifics, these should not be construed as limitations on the scope of the disclosure or of what may be claimed, but rather as descriptions of features specific to particular implementations of the disclosure. Certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. Accordingly, the claimed invention is limited only by the claims that follow below.

What is claimed is:

1. A method of bioremediation of an oil spill, the method comprising:
examining an oil spill to determine borders of an area of the oil spill;
selecting a first deployment means for a bioremediation agent, the bioremediation agent including an oil-digesting bacteria suspended in a non-toxic semi-insoluble protein product to digest oil of the oil spill; and
with the first selected deployment means, deploying the bioremediation agent over the area of the oil spill to couple the oil-digesting bacteria to the oil of the oil spill.

2. The method of claim 1, wherein
the non-toxic semi-insoluble protein product is semi-insoluble casein.

3. The method of claim 1, further comprising:
suspending bacterial nutrients in the non-toxic semi-insoluble protein product to grow the oil-digesting bacteria.

4. The method of claim 1, further comprising:
suspending a gas in pockets within the non-toxic semi-insoluble protein product to adjust the buoyancy of the bioremediation agent towards a surface of water.

5. The method of claim 4, wherein
the gas is one or more of air, helium, hydrogen, oxygen, methane, and ammonia.

6. The method of claim 1, further comprising:
suspending an inert material with a specific gravity greater than water within the non-toxic semi-insoluble protein product to adjust the buoyancy of the bioremediation agent down away from a surface of water.

7. The method of claim 6, further comprising:
selecting the specific gravity of the inert matter to sink the bioremediation agent to the same depth as a submerged oil plume of the oil spill; and
deploying the bioremediation agent over the oil plume of the oil spill.

8. The method of claim 4, wherein
the non-toxic semi-insoluble protein product is semi-insoluble casein.

9. The method of claim 1, further comprising:
ascertaining the effectiveness of the oil-digesting bacteria; and
if the deployment of the oil-digesting bacteria was ineffective, then further deploying the bioremediation agent over the area of the oil spill to couple additional oil-digesting bacteria to the oil of the oil spill.

10. The method of claim 1, further comprising:
selecting a second deployment means for the bioremediation agent over an area of an eco-system,
with the second selected deployment means, deploying the bioremediation agent over the area of the eco-system to couple the oil-digesting bacteria to oil from the oil spill.

11. The method of claim 1, wherein
a processor executes instructions to examine the oil spill.

12. The method of claim 1, wherein
a processor executes instructions stored in a storage device to select the deployment means of the bioremediation agent.

13. The method of claim 1, wherein
the deployment means is one or more of a spreader, a truck, a ship, and an aircraft.

14. The method of claim 6, wherein
the water is fresh water.

15. The method of claim 6, wherein
the water is salt water.

16. A method for bioremediation of an oil spill, the method comprising:
deploying a bioremediation agent over an area of the oil spill, the bioremediation agent comprising oil-digesting bacteria suspended in a non-toxic semi-insoluble protein product having micro-pores;
absorbing oil of the oil spill through the micro-pores in the non-toxic semi-insoluble protein product of the bioremediation agent;
supporting the growth and proliferation of the oil-digesting bacteria suspended in the non-toxic semi-insoluble protein product; and
digesting the absorbed oil with the oil-digesting bacteria.

17. The method of claim 16, further comprising:
adjusting the buoyancy of the bioremediation agent with respect to a specific gravity of water.

18. The method of claim 16, wherein
the non-toxic semi-insoluble protein product is semi-insoluble casein.

19. The method of claim 16, further comprising
dissolving the non-toxic semi-insoluble protein product into water after a predetermined period of time.

* * * * *